United States Patent [19]
Wermuth et al.

[11] Patent Number: 5,872,119
[45] Date of Patent: Feb. 16, 1999

[54] 2-NAPHTHAMIDE DERIVATIVES AND THEIR THERAPEUTIC APPLICATIONS

[75] Inventors: Camille-Georges Wermuth, Strasbourg; Andre Mann, Ostwald; Fabrice Garrido, Strasbourg; Jeanne-Marie Lecomte; Jean-Charles Schwartz, both of Paris; Pierre Sokoloff, Le Plessis Bouchard, all of France

[73] Assignees: Institut National De La Sante et De La Recherche Medicale—INSERM; Societe Civile Brioprojet, both of France

[21] Appl. No.: 762,782

[22] Filed: Dec. 10, 1996

[30] Foreign Application Priority Data

Dec. 11, 1995 [FR] France ................... 95 14654

[51] Int. Cl.⁶ .................. A61K 31/495; A61K 31/50; C07D 401/00; C07D 413/00
[52] U.S. Cl. ............ 514/254; 514/252; 514/255; 544/360; 544/368; 544/376; 544/393
[58] Field of Search ................ 544/360, 368, 544/376, 393; 514/252, 254, 255

[56] References Cited

U.S. PATENT DOCUMENTS

| | | | |
|---|---|---|---|
| 4,975,439 | 12/1990 | Van Daele et al. | 544/360 |
| 5,010,078 | 4/1991 | Abou-Gharbia et al. | 544/360 |
| 5,106,849 | 4/1992 | Abou-Gharbia et al. | 514/247 |
| 5,254,552 | 10/1993 | Abou-Gharbia et al. | 514/252 |
| 5,395,835 | 3/1995 | Glase et al. | 514/254 |

FOREIGN PATENT DOCUMENTS

| | | |
|---|---|---|
| 539281 | 4/1993 | European Pat. Off. |
| 709375 | 5/1995 | European Pat. Off. |
| 9321179 | 10/1993 | WIPO |

OTHER PUBLICATIONS

Emonds–Alt et al., Bioorganic & Med, Chem. Letters, (1993)vol. 3, No. 5, pp. 925–930, 1993.
Glase et al., Bioorganic & med. Chem. Letters, (1996), vol. 6, No. 12, pp. 1361–1366, 1996.
Nilsson et al., J. Med. Chem. (1997), 40, 833–840, 1997.

*Primary Examiner*—S. Mark Clardy
*Assistant Examiner*—Sabiha N. Qazi
*Attorney, Agent, or Firm*—Bierman, Muserlian and Lucas

[57] ABSTRACT

The invention related to 2-naphthamide derivatives, in the form of bases or of salts, corresponding to the following general formula (I):

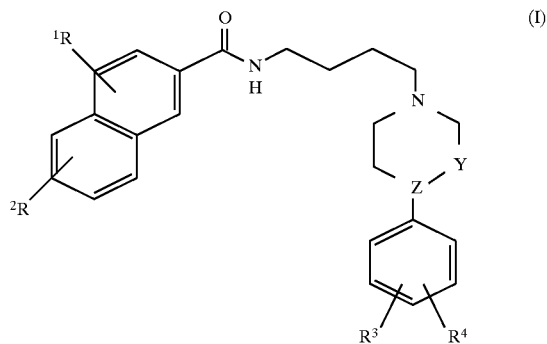

in which:

the Z—Y entity represents an N—CH$_2$, C=CH or CH—CH$_2$ group;

$R^1$ represents a hydrogen, fluorine, bromine or iodine atom or a hydroxyl, methoxy, nitrile or nitro group;

$R^2$ represents a hydrogen or bromine atom or a hydroxyl, methoxy, nitrile or nitro group;

the $R_1$ and $R^2$ substituents both being situated on the same ring of the naphthamide unit or each being situated on one of the rings;

$R^3$ and $R^4$ can be identical or different and each independently represent a hydrogen or chlorine atom or a methoxy or methyl group or an electron-withdrawing group.

The invention also relates to their therapeutic applications as partial agonists of the dopamine D$_3$ receptor.

The invention applies more particularly to the treatment of neuropsychiatric conditions involving the dopamine D$_3$ receptor, in particular psychotic and depressive states, to the treatment of drug-dependence states or to the treatment of disorders of a sexual nature.

15 Claims, No Drawings

2-NAPHTHAMIDE DERIVATIVES AND THEIR THERAPEUTIC APPLICATIONS

The present invention relates to new chemical compounds derived from 2-naphthamides and to their therapeutic applications, in particular as selective dopaminergic agents.

Many phenylpiperazine derivatives are known and used for their activity with respect to the central nervous system, in particular for their neuroleptic properties.

Phenylpiperazines are known essentially as serotoninergic agents.

As regards the dopamine receptors, it has been shown that some arylpiperazine derivatives exhibit a higher affinity for the dopamine $D_3$ receptor, in comparison with other dopamine receptors (Murray P. J. et al., Bioorganic & Medicinal Chemistry Letters, vol. 5, No. 3, pp 219–222 (1995)).

According to this document, these compounds, which exhibit a degree of selectivity with respect to the dopamine $D_3$ receptor in comparison with other receptors, could be used to verify the hypothesis that a selective antagonist of the dopamine $D_3$ receptor could furnish an effective antipsychotic agent which does not have extra-pyramidal side effects.

Moreover, it has been shown that some naphthamide derivatives behaved as pure antagonists of the $D_3$ receptor and could therefore be used for the preparation of medicaments which are antagonists of dopamine by blockage of the $D_3$ receptor (French Patent Application No. 91 13103).

Recently, naphthamide derivatives of arylpiperazines have also been described, in U.S. Pat. No. 5,395,835, as selective antagonists of the dopamine $D_3$ receptor. These compounds are useful as antipsychotic agents and for the treatment of disorders related to dopaminergic blockage.

It is in this state of knowledge that the Inventors have demonstrated, in an entirely surprising and unexpected way, that 2-naphthamide derivatives of formula (I) given below exhibited a strong affinity for dopaminergic receptors and in particular for the $D_3$ receptor and that they behaved selectively as powerful partial agonists of dopamine at the $D_3$ receptor.

Thus, the subject of the present invention is 2-naphthamide derivatives, in the form of bases or of salts, corresponding to the general formula (I):

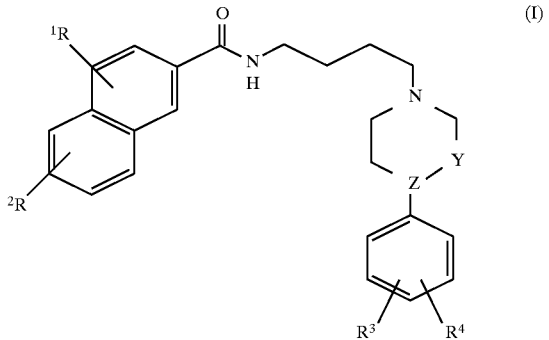

in which:

the Z—Y entity represents an N—CH$_2$, C=CH or CH—CH$_2$ group;

$R^1$ represents a hydrogen, fluorine, bromine or iodine atom or a hydroxyl, methoxy, nitrile or nitro group;

$R^2$ represents a hydrogen or bromine atom or a hydroxyl, methoxy, nitrile or nitro group;

the $R_1$ and $R_2$ substituents both being situated on the same ring of the naphthamide unit or each being situated on one of the rings;

$R^3$ and $R^4$ can be identical or different and each independently represent a hydrogen or chlorine atom or a methoxy or methyl group or an electron-withdrawing group.

A further subject of the invention is pharmaceutical compositions comprising a therapeutically effective amount of at least one derivative of abovementioned formula (I), in the base form or in the form of a pharmaceutically acceptable salt, in combination with a pharmaceutically acceptable vehicle or excipient.

It further relates to medicaments acting as partial agonists of the dopamine $D_3$ receptor comprising, as active principle, at least one derivative of abovementioned formula (I) and to the use of the said derivatives for the preparation of such medicaments.

The derivatives according to the invention are represented by the general formula (I). These compounds are novel.

Naphthamide derivatives of arylpiperazines may be found in the literature (abovementioned U.S. Pat. No. 5,395,835) but, in these compounds, the piperazine unit is separated from the naphthamide unit by a chain containing 2 carbon atoms whereas, according to the invention, the chain exhibits 4 carbon atoms.

The derivatives according to the invention can be provided in the form of free bases or in the form of salts, in particular in the form of addition salts with physiologically acceptable acids, and the invention also applies to these various forms.

According to the invention, the derivatives for which the Z—Y entity represents an N—CH$_2$ group constitute preferred derivatives.

Mention may be made, as particularly preferred derivatives according to the invention, of the following compounds:

N-[4-(4-(2-methoxyphenyl)piperazinyl)butyl]-1-methoxy-4-nitro-2-naphthamide;

N-[4-(4-phenyl-1,2,3,6-tetrahydropyridinyl)butyl]-2-naphthamide;

N-[4-(4-phenylpiperidinyl)butyl]-2-naphthamide;

N-[4-(4-(2-methoxyphenyl)piperazinyl)butyl]-1-methoxy-4-cyano-2-naphthamide;

N-[4-(4-(2-methoxyphenyl)piperazinyl)butyl]-2-naphthamide;

N-[4-(4-(2-chlorophenyl)piperazinyl)butyl]-3-methoxy-2-naphthamide;

N-[4-(4-(2-chlorophenyl)piperazinyl)butyl]-2-naphthamide;

N-[4-(4-(3-chlorophenyl)piperazinyl)butyl]-2-naphthamide;

N-[4-(4-phenylpiperazinyl)butyl]-2-naphthamide;

N-[4-(4-(2-methoxyphenyl)piperazinyl)butyl]-1-methoxy-2-naphthamide oxalate.

The derivatives of formula (I) according to the present invention can be prepared by known methods (W. Adcock et al., Aust. J. Chem., 1965, 18, 1351).

The suitably substituted acid part (2-naphthoic acid) is converted to the mixed anhydride with isobutyl chloroformate in acetone or any other solvent, in basic medium, and reacted with the desired amine as shown in the following reaction scheme:

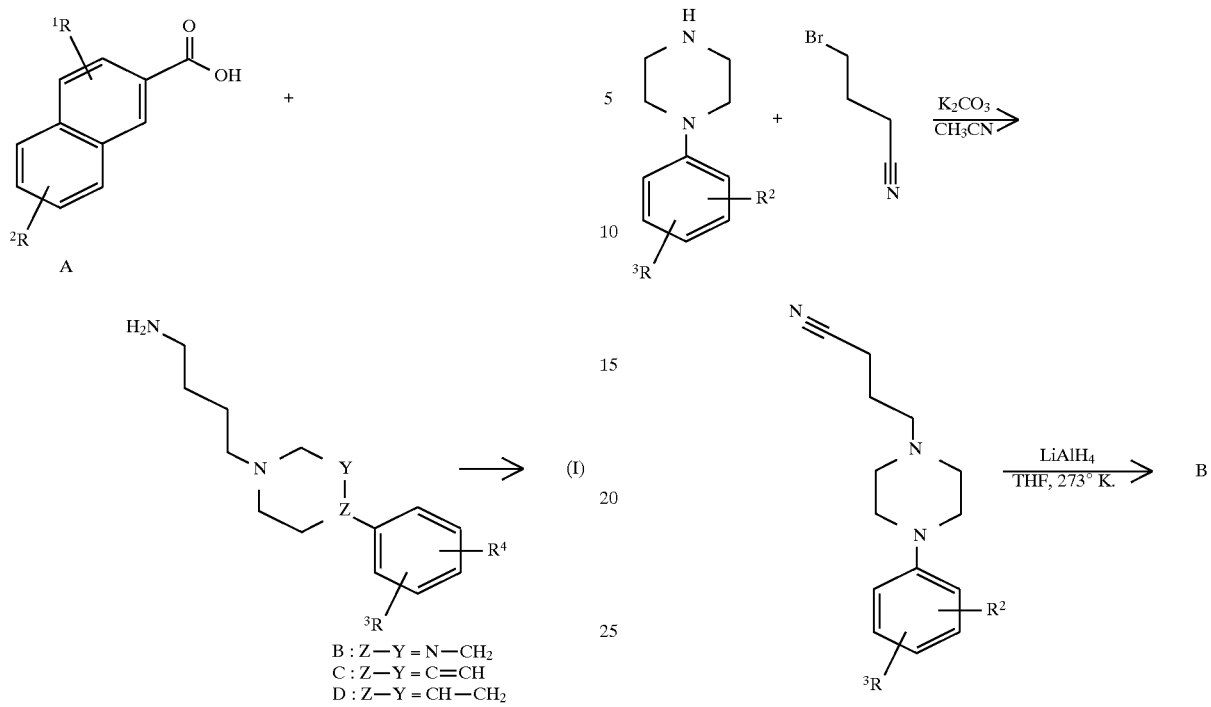

Other methods for activating the carboxyl functional group can also be used; in fact, any method for the preparation of an amide is suitable, including the use of the corresponding acid chlorides.

Aminopiperazines of type B are obtained by conventional methods, often starting from commercially available phenylpiperazines, by alkylation by means of chlorobutyronitrile in basic medium in an alcoholic solvent. The nitrile functional group is then reduced to a primary amine, either with LiAlH$_4$ or by catalytic hydrogenation in the presence of palladium (Pd)-on-charcoal.

Aminobutylphenyltetrahydropyridines of type C or aminobutylphenylpiperidines of type D are also obtained by conventional methods, either from commercially available products or from N-Boc-4-piperidone (where Boc means tert-butoxycarbonyl), which is reacted with a phenylmagnesium derivative and which is then dehydrated in order to obtain the corresponding tetrahydropyridine. The corresponding piperidine is obtained by catalytic hydrogenation of the latter. The t-butoxycarbonyl (Boc) protection is hydrolysed in acid medium and the nitrogen is alkylated with bromobutyronitrile in basic medium in the same way as above. The scheme for the preparation of the compounds C and D is given below:

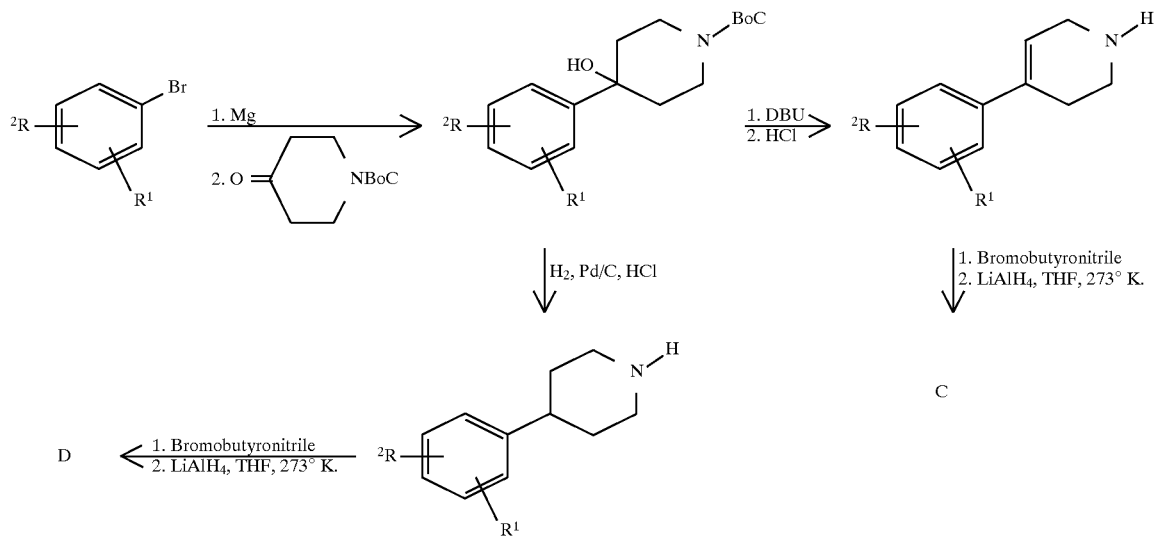

EXAMPLES

Example 1

Preparation of N-[4-(4-(2-methoxyphenyl)-piperazinyl)butyl]-1-methoxy-4-nitro-2-naphthamide (Do 885)

120 mg of 1-methoxy-4-nitronaphthalene-2-carboxylic acid A (prepared as indicated below in a)) are dissolved in 15 ml of anhydrous acetone in a 25 ml two-necked flask. 2.5 equivalents of triethylamine are added and the mixture is cooled to -15° C. by means of a dry ice/acetone bath. 1.05 equivalents of isobutyl chloroformate are then added to the mixture, which is allowed to react for 1 hour at −15° C. 1.05 equivalents of N-(4-aminobutyl)-N'-(2-methoxyphenyl) piperazine B (prepared as indicated below in b)) are then added and reaction is allowed to take place for 2 hours at room temperature under an inert atmosphere. The triethylamine In hydrochloride is filtered off and the filtrate is evaporated to dryness. The residue is taken up in a small amount of ethyl acetate and the naphthamide is purified by chromatography on a silica column (eluent: AcOEt/MeOH 90/10). The naphthamide is crystallized from diethyl ether. 85 mg of yellow crystals are obtained. Y=37%. M.p.=109° C. $^1$H NMR (CDCl$_3$):1.59–1.73 (m, 2H, —CH$_2$—), 2.47–2.66 (m, 6H, —H$_2$C—CH$_2$—CH$_2$—), 3.02–3.20 (m, 4H, —CH$_2$—CH$_2$—), 3.58–3.61 (m, 4H, —H$_2$C—CH$_2$—), 3.86 (s, 3H, OCH$_3$, phenyl), 4.08 (s, 3H, OCH$_3$, naphthyl), 6.79–7.03 (m, 4H, —HC—CH—CH—CH—, phenyl), 7.68–7.85 (m, 2H, —HC—CH—), 8.27–8.31 (d, 1H, —CH—), 8.62–8.66 (d, 1H, —CH—), 8.87 (s, 1H, —CH—). Analysis C$_{27}$H$_{32}$N$_4$O$_5$ Cal. % C 65.84, % H 6.55, % N 11.37
Fd. % C 66.25, % H 6.43, % N 11.12 a) Preparation of 1-methoxy-4-nitro-2-naphthoic acid (A)

Methyl ester of 1-methoxy-2-naphthoic acid 1.88 g (10 mmol) of 1-hydroxy-2-naphthoic acid are suspended in 50 ml of methyl ethyl ketone. 2.76 g (2 equivalents) of anhydrous potassium carbonate are added and then 2.51 g (2 equivalents) of dimethyl sulphate, in solution in the solvent, are added dropwise. The mixture is heated at reflux with stirring overnight, then, after cooling, the excess potassium carbonate is filtered off and the filtrate is concentrated. The evaporation residue is taken up in water and extracted a number of times with ethyl acetate. The organic phase is washed with water, dried over sodium sulphate and then evaporated. Purification is carried out by chromatography on a silica column (eluent: hexane/ethyl acetate 90/10). A golden oil is obtained. Y=82%. $^1$H NMR (CDCl$_3$):4.00 (3H, s, CO$_2$CH$_3$), 4.08 (3H, s, OCH$_3$, 7.55–7.63 (3H, m, HC—CH—CH), 7.83–7.90 (2H, m, HC—CH), 8.27–8.32 (1H, m, CH). $^{13}$C NMR (CDCl$_3$):52.1 (OCH$_3$), 58.3 (OCH$_3$), 166.4 (C=O), 158.1 (C—O, α), 119.0 (C—C=O, β), 126.3 (C—H, β), 123.4 (C—H, α), 128.2 (C—H, α), 128.4 (C—H, β), 127.7 (C—H, β), 127.6 (C—H, α), 128.6 (C—C, γ), 136.6 (C—C, γ)

Methyl ester of 1-methoxy-4-nitro-2-naphthoic acid 2 g of methyl ester of 1-methoxy-2-naphthoic acid are dissolved in 15 ml of glacial acetic acid. 1.2 equivalents of concentrated nitric acid, in solution in glacial acetic acid, are added dropwise and reaction is allowed to take place for 4 hours at room temperature with good stirring. The reaction mixture is slowly hydrolysed in ice. The methyl ester of 1-methoxy-4-nitro-2-napthoic acid precipitates. The precipitate is filtered off, washed a number of times with ice-cold water, then redissolved in ethyl acetate, washed with water and then with a saturated potassium carbonate solution (note 1), in order to remove the residual acetic acid, and finally washed with water. The mixture is dried over sodium sulphate and concentrated. Purification is carried out by chromatography on a silica column (eluent: hexane/CH$_2$Cl$_2$ 60/40). Yellow crystals:Y=89%. Melting p.:110° C. $^1$H NMR (CDCl$_3$):4.02 (3H, s, —CO$_2$CH$_3$), 4.14 (3H, s, —OCH$_3$), 7.65–7.86 (2H, m, —HC—CH), 8.39–8.43 (1H, dd, —CH), 8.62–8.66 (1H, dd, —CH), 8.74 (1H, s, —CH). $^{13}$C NMR (CDCl$_3$):52.7 (—OCH$_3$), 64.0 (—OCH$_3$), 164.5 (>C=O), 162.9 (>C—O, α), 116.9 (>C—C=O, β), 124.4 (>C—H, β), 129.5 (>C—NO$_2$, α), 141.5 (>C—C, γ), 123.6 (>C—H, α), 131.8 (>C—H, β), 127.9 (>C—H, β), 126.6 (>C—H, α), 128.2 (>C—C, γ). Note 1:It is preferable not to use sodium hydroxide because it forms a highly coloured complex which is difficult to remove. It is important to thoroughly wash the precipitate beforehand in order to remove as much as possible of the acid as the neutralization of acetic acid by K$_2$CO$_3$ gives off carbon dioxide.

1-Methoxy-4-nitro-2-naphthoic acid (A)

750 mg of methyl ester of 1-methoxy-4-nitro-2-naphthoic acid are dissolved in 20 ml of methanol. 1.5 equivalents of sodium hydrogencarbonate are added and the mixture is heated at reflux for 10 hours. The mixture is concentrated and the residue is taken up in water. Extraction is carried out with ether in order to remove the organic impurities and the aqueous phase is acidified to pH=2 with 5N hydrochloric acid. A yellowish-white precipitate is obtained. Extraction is carried out with ethyl acetate, washing with water is carried out 3 times, drying is carried out over sodium sulphate and the mixture is concentrated. The acid is crystallized from pentane. Purification is carried out by hot recrystallization from water and addition of active charcoal in order to remove the impurities. Yellowish- white crystals. Y=94%.

b) Preparation of N-(4-aminobutyl)-N'-(2-methoxyphenyl)piperazine (B)

N-(2-methoxyphenyl)-N'-(3-cyanopropyl) piperazine 8 g of N-(2-methoxyphenyl)piperazine are suspended in 150 ml of acetonitrile. 2.5 equivalents of anhydrous potassium carbonate are added and then 1.05 equivalents of 4-bromobutyronitrile, in solution in acetonitrile, are added dropwise. The mixture is heated at reflux for 10 hours and then filtered and the filtrate is concentrated. The residue is taken up in ethyl acetate and washed 3 times with water. The organic phase is extracted with a 1M hydrochloric acid solution and the acid phase is washed with ethyl acetate. The acid phase is neutralized with 28% aqueous ammonia to pH>11. Extraction is carried out with ethyl acetate, the organic phase is washed with water and dried over anhydrous sodium sulphate and the mixture is concentrated. The nitrile is crystallized from hexane and recrystallized while hot from the same solvent. 6.8 g of nitrile are obtained. Y=75%. M.p.=74° C. $^1$H NMR (CDCl$_3$):1.80–1.94 (m, 2H, —CH$_2$—), 2.43–2.57 (m, 4H, —CH$_2$—CH$_2$—) 2.62–2.67 (broad t, 4H, —CH$_2$—N<), 3.09 (broad s, 4H, >N—CH$_2$—), 3.87 (s, 3H, —OCH$_3$), 6.85–7.04 (m, 4H, —CH—CH—CH—CH—). $^{13}$C NMR (CDCl$_3$):14.9 (—CH$_2$—CH$_2$—C≡N), 22.7 (—CH$_2$—C≡N), 50.5 (—CH$_2$—N-(CH$_2$)$_2$—), 53.2 (>C—N-(CH$_2$)$_2$—), 55.3 (—OCH$_3$), 56.3 (>N—

$CH_2$—), 111.1 (—CH—C—$OCH_3$), 118.1 (—CH—CH—C—$OCH_3$), 119.8 (—C≡N), 120.9 (—CH—C—N<), 122.9 (—CH—CH—C—N<), 141.1 (>C—N<), 152.2 (—C—$OCH_3$).

—N-(4-Aminobutyl)-N'-(2-methoxyphenyl) piperazine (B)

1.2 g of lithium aluminium hydride are suspended in small portions (exothermic dissolution) in 50 ml of anhydrous diethyl ether (freshly distilled over sodium). 5 g of N-(2-methoxyphenyl)-N'-(3-cyanopropyl) piperazine, in solution in anhydrous tetrahydrofuran (THF), are added dropwise and heating is then carried out at reflux for 2 hours. The mixture is hydrolysed with a mixture of 5 ml of water in 25 ml of THF and allowed to stand overnight in order to enable the precipitate to agglomerate. The precipitate is filtered on celite, the filtrate is dried over anhydrous sodium sulphate and the filtrate is concentrated. Y=81%. $^{13}C$ NMR ($CDCl_3$):24.3 (—$CH_2$—$CH_2$—$CH_2$—$NH_2$), 31.9 (—$CH_2$—$CH_2$—$NH_2$), 42.2 (—$CH_2$—$NH_2$), 50.6 (—$CH_2$—N-$(CH_2)_2$—), 53.4 (>C—N—$(CH_2)_2$—), 55.3 (—$OCH_3$), 58.6 (>N—$CH_2$—), 111.1 (—CH—C—$OCH_3$), 118.1 (—CH—CH—$COCH_3$), 120.9 (—CH—C—N<), 122.8 (—CH—CH—C—N<), 141.3 (>C—N<), 152.2 (—C—$OCH_3$).

Example 2

Preparation of N-[4-(4-phenyl-1,2,3,6-tetrahydropyridinyl)butyl]-2-naphthamide (Do 911)

250 mg of naphthalene-2-carboxylic acid A (2-naphthoic acid) are suspended in 20 ml of anhydrous dichloromethane (freshly distilled over $CaH_2$). 1.2 equivalents of oxalyl chloride are added at 0° C. and then 2 drops of anhydrous dimethylformamide are added (to catalyse the chlorination reaction) and reaction is then allowed to take place at room temperature for 1 hour under an inert atmosphere (argon) and with vigorous stirring. The mixture is concentrated in order to remove the solvent and the excess oxalyl chloride and then the acid chloride formed is redissolved in 20 ml of dichloromethane. 1.05 equivalents of N-(4-aminobutyl)-4-phenyl-1,2,3,6-tetrahydropyridine C (prepared as indicated below in c)) are added and reaction is allowed to take place for 2 hours at room temperature under an inert atmosphere (argon). The mixture is concentrated and the residue is taken up in a 3M aqueous hydrochloric acid solution. The acid phase is washed with ethyl acetate and then the aqueous phase is neutralized with a 32% aqueous ammonia solution to pH>11. Extraction is carried out with ethyl acetate, the organic phase is washed a number of times with water and dried over sodium sulphate and the mixture is concentrated. The residue is crystallized from a 50/50 ether/hexane mixture. 280 mg of white crystals are obtained. Y=50%. M.p.=172° C. $^1H$ NMR ($CDCl_3$):1.73–1.83 (m, 4H, —$H_2C$—$CH_2$—), 2.51–2.58 (t, 4H, —$H_2C$—$CH_2$—), 2.69–2.75 (t, 2H, —$CH_2$—), 3.11–3.16 (q, 2H, —$CH_2$—), 3.52–3.58 (2H, q, —$CH_2$—), 6.01–6.04 (1H, t, —CH=), 7.24–7.35 (5H, m, —$(CH)_5$<, phenyl), 7.39–7.55 (m, 2H, >HC—CH<, naphthyl), 7.78–7.85 (4H, m, >HC—CH—CH—CH—CH<, naphthyl), 8.24 (1H, s, >CH—, naphthyl).

c) Preparation of N-(4-aminobutyl)-4-phenyl-1,2,3,6-tetrahydropyridine (C)

4-(4-Phenyl-1,2,3,6-tetrahydropyridinyl)-butyronitrile 5 g of 4-phenyl-1,2,3,6-tetrahydropyridine hydrochloride (very toxic compound: New Engl. J. Med., 1983, 309, 310; Science, 1983, 219, 979; Psychiatry Res., 1979, 1, 249) and then 100 ml of acetonitrile are introduced into a 250 ml round-bottomed flask. 2.5 equivalents of anhydrous potassium carbonate are added and then 1.05 equivalents of 4-bromobutyronitrile, in solution in acetonitrile, are added dropwise. The mixture is heated at reflux for 16 hours and then filtered, the precipitate is washed with acetone and the filtrate is concentrated. The residue is taken up in ethyl acetate and washed 3 times with water. The organic phase is extracted with a 3M hydrochloric acid solution and the acid phase is washed with ethyl acetate. The acid phase is neutralized with 28% aqueous ammonia to pH>11. Extraction is carried out with ethyl acetate, the organic phase is washed with water and dried over anhydrous sodium sulphate and the mixture is concentrated. The nitrile is purified by chromatography on a silica column (eluent: ethyl acetate/hexane 80/20). White crystals are obtained. M.p.=57–59° C. Y=79%. $^1H$ NMR ($CDCl_3$, 330° K.):1.81–1.95 (m, 2H, —$CH_2$—, 2.40–2.48 (t, 2H, —$CH_2$—), 2.54–2.60 (t, 4H, —$H_2C$—$CH_2$—), 2.67–2.72 (t, 2H, —$CH_2$—), 3.12–3.17 (q, 2H, —$CH_2$—), 6.06–6.09 (m, 1H, —CH=), 7.24–7.44 (m, 5H, phe). $^{13}C$ NMR ($CDCl_3$):14.7 (—$CH_2$—$CH_2$—C≡N), 22.8 (—$CH_2$C≡N), 27.7 (>C—$CH_2$—$CH_2$—N<, pyrid), 50.0 (—$CH_2$—$CH_2$—N<, pyrid), 52.9 (=CH—$CH_2$—N<, pyrid), 55.9 (>N—$CH_2$—), 119.6 (—CN), 121.3 (>CH—), 124.6 (=CH—, pyri), 126.8 (>$(CH)_2$—), 128.1 (>$CH)_2$—), 134.7 (>C=C—, pyri), 140.4 (>C<).

N-(4-Aminobutyl)-4-phenyl-1,2,3,6-tetrahydropyridine (C) 1.8 g of lithium aluminium hydride are suspended in small portions (exothermic dissolution) in 50 ml of anhydrous THF (freshly distilled over sodium). 4.5 g of 4-(4-phenyl-1,2,3,6-tetrahydropyridinyl)butyronitrile, in solution in THF, are added dropwise at 0° C. and then reaction is allowed to take place at 0° C. for 3 hours with good stirring. The mixture is hydrolysed with a mixture of 5 ml of water in solution in 50 ml of THF and the combined mixture is allowed to stand overnight in order to agglomerate the precipitate. The precipitate is filtered on celite and the filtrate is dried over anhydrous sodium sulphate and concentrated. The residue is distilled under pump vacuum. A colourless oil is obtained. Y=86%. $^1H$ NMR ($CDCl_3$):1.26 (bs, 2H, —$NH_2$), 1.43–1.66 (m, 4H, —$H_2C$—$CH_2$—), 2.44–2.51 (t, 2H, —$CH_2$—) 2.59 (b s, 2H, —$CH_2$—), 2.68–2.76 (m, 4H, —$CH_2$—$CH_2$—) 3.15–3.19 (d, 2H, —$CH_2$—), 3.72–3.78 (q, 2H, —$CH_2$—), 6.06 (q, 1H, —CH=), 7.22–7.41 (m, 5H, phe). $^{13}C$ NMR ($CDCl_3$):24.6 (—$CH_2$—$CH_2$—$CH_2$—$NH_2$), 28.1 (—$CH_2$—$CH_2$—$NH_2$), 31.9 (—$CH_2$—$CH_2$—N<, pyrid), 42.2 (—$CH_2$—$NH_2$), 50.4 (—$CH_2$—$CH_2$—N<, pyrid), 53.3 (=CH—$CH_2$—N<), 58.3 (>N—$CH_2$—), 121.9 (>CH—), 124.9 (>$CH)_2$—), 126.9 (>$(CH)_2$—), 128.2 (<C=CH—, pyrid), 135.0 (>C=CH—, pyrid), 140.9 (>C<).

Example 3

Preparation of N-[4-(4-phenylpiperidinyl)-butyl]-2-naphthamide (Do 912)

120 mg of N-[4-(4-phenyl-1,2,3,6-tetrahydropyridinyl) butyl]-2-naphthamide obtained according to Example 2 are dissolved in 20 ml of methanol in a 100 ml Parr bottle. A spatula tip of Pd/C (palladium-on-charcoal) is added and hydrogenation is carried out with the Parr apparatus for 6 hours under a pressure of 60 p.s.i.. The catalyst is filtered off and rinsed with methanol and the filtrate is concentrated. Purification is carried out by chromatography on a silica column (eluent: ethyl acetate/methanol 90/10). Crystallization is carried out from hexane. 110 mg of white crystals are obtained. Y=91%. M.p.=143–144° C. $^1H$ NMR ($CDCl_3$, 330° K.):1.76–1.86 (m, 7H, —$H_2C$—$CH_2$—$CH_2$—CH<), 2.06–2.14 (m, 2H, —CH$_2$—), 2.48–2.54 (m, 4H, —H$_2$C—CH$_2$—), 3.07–3.13 (m, 2H, —CH$_2$—), 3.56–3.60 (q, 2H, —CH$_2$—), 6.94 (b.s., 1H, —NH), 7.12–7.29 (m, 5H, >(CH)$_5$—, phenyl), 7.51–7.55 (m, 2H, >HC—CH<), 7.84–7.93 (m, 4H, >HC—CH—CH—CH<), 8.30 (s, 1H, >CH—).

Analysis C$_{26}$H$_{30}$N$_2$O
Calc. % C 80.79, % H 7.82, % N 7.25
Fd. % C 80.66, % H 7.89, % N 7.22

Example 4

Preparation of N-[4-(4-(2-methoxyphenyl)-piperazinyl)butyl] -1-methoxy-4-cyano-2-naphthamide (883)

120 mg of 1-methoxy-4-cyanonaphthalene-2-carboxylic acid (prepared as in Example 1a)) are dissolved in 20 ml of anhydrous acetone. 2.5 equivalents of triethylamine are added and the mixture is cooled to –15° C. by means of a dry ice/acetone bath. 1.05 equivalents of isobutyl chloroformate are added and reaction is allowed to take place for 1 hour at –15° C. 1.05 equivalents of N-(4-aminobutyl)-N'-(2-methoxyphenyl)piperazine (prepared as in Example 1b)) are then added and reaction is allowed to take place for 2 hours at room temperature under an inert atmosphere. The triethylamine hydrochloride is filtered off and the filtrate is evaporated to dryness. The evaporation residue is taken up in a small amount of ethyl acetate and the naphthamide is purified by chromatography on a silica column (eluent: ethyl acetate/methanol 90/10). The naphthamide is crystallized from diethyl ether. 76 mg of white crystals are obtained. Y=23%. M.p.=128° C. $^{13}$C NMR (CDCl$_3$):24.4 (—CH$_2$—CH$_2$—CH$_2$NH—), 27.5 (—CH$_2$—CH$_2$—NH—), 39.9 (CH$_2$—NH—), 50.4 (—CH$_2$—N—(CH$_2$)$_2$—), 53.3 (>C—N—(CH$_2$)$_2$—), 55.1 (—OCH$_3$, phenyl), 58.0 (>N—CH$_2$—), 63.4 (—OCH$_3$, naphthyl), 106.7 (—CH—C=—N, α), 111.0 (—CH—C—OCH3, phenyl), 116.9 (—C—N), 117.9 (—CH—CH—C—OCH$_3$phenyl), 120.8 (—CH—C—N<, phenyl), 122.5 (>C—C=O, β), 122.8 (—CH—CH—C—N<, phenyl), 123.6 (—CH—CH—C—C—OCH$_3$, β), 125.5 (—CH—C—C—OCH$_3$, α), 127.5 (—C—C—OCH$_3$, γ), 128.0 (—CH—C—C=N, α), 130.1 (—CH—C—C=O, β), 134.4 (—CH—CH—C—C—C=N, β), 134.7 (—C—C=N, γ) , 141.1 (>C—N<, phenyl), 152.1 (—C—OCH$_3$, phenyl), 158.4 (—C—OCH$_3$, α), 163.8 (>C=O).

Example 5

N-[4-(4-(2-Methoxyphenyl)piperazinyl)butyl]-2-naphthamide

M.p.=121° C., C$_{26}$H$_{31}$N$_3$O$_2$(DO 897)

Example 6

N-[4-(4-(2-Chlorophenyl)piperazinyl)butyl]-3-methoxy- 2 -naphthamide

M.p.=86° C., C$_{26}$H$_{30}$N$_3$O$_2$Cl (DO 917)

Example 7

N-[4-(4-(2-Chlorophenyl)piperazinyl)butyl]-2-naphthamide

M.p.=107°–109° C., C$_{25}$H$_{28}$ClN$_3$O (DO 910)

Example 8

N-[4-(4-(3-Chlorophenyl)piperazinyl)butyl]-2-naphthamide

M.p.=150°–152° C., C$_{25}$H$_{29}$N$_3$O (DO 908)

Example 9

N-[4-(4-(Phenylpiperazinyl)butyl]-2-naphthamide

M.p.=164° C., C$_{25}$H$_{29}$N$_3$O (DO 905)

Example 10

N-[4-(4-(2-Methoxyphenyl)piperazinyl)butyl]-1-methoxy-2-naphthamide oxalate

M.p.=164° C., C$_{27}$H$_{34}$N$_3$O$_3$·C$_2$H$_2$O$_4$ (897a)

BIOLOGICAL ACTIVITY

The activity of the derivatives of formula (I) according to the invention was evaluated with respect to cells expressing human recombinant dopaminergic receptors, the degree of stimulation of which can be determined by measuring the incorporation of [$^3$H]-thymidine: CHO cells expressing the D$_2$S receptor and NG 108–15 cells expressing the D$_3$ receptor (Pilon et al., Eur. J. Pharmacol. Mol. Pharmacol. Sect., 1994, 268: 129–139; Sautel et al. Neuroreport, 1995, 6: 329–332).

Among these derivatives, some exhibit a much greater affinity for the D$_3$ receptor in comparison with the D$_2$ receptor.

Whereas compounds of the nafadotride type (abovementioned French Patent Application No. 91 13103) behave as pure antagonists of the D$_3$ receptor, the Inventors have discovered that, unexpectedly, the compounds of the present invention behave as powerful partial agonists of dopamine at the D$_3$ receptor, their intrinsic activity varying between 50% and 80% (dopamine=100%). Thus it is that the compound of Example 5 exhibits an intrinsic activity of 60% and that its 50% effective concentration is 3 nM. This same compound exhibits an apparent affinity with respect to the D$_2$ receptor which is 25 times smaller than with respect to the D$_3$ receptor: it consequently constitutes a very selective (partial) agonist of the latter.

What is more, the Inventors have also shown that minimum structural differences among the compounds described here can result in significant variations in the selectivity and the intrinsic activity of the molecules.

For example, when R$_3$ and R$_4$ each represent a methoxy group, this disubstitution causes the D$_3$ receptor/D$_2$ receptor selectivity to be lost, in comparison with a monosubstitution. Moreover, the presence of a chlorine substituent (R$_3$ or R$_4$) greatly decreases the affinity of the derivative (I) for the D$_3$ receptor.

These properties lead to therapeutic applications which cannot yet be envisaged with existing dopaminergic agents. In fact, the high selectivity of the molecules allows selective activation of the dopaminergic transmissions of the limbic regions involved in emotional and cognitive processes (which express the D$_3$ receptor), without interference with the dopaminergic transmissions of the extra-pyramidal, antehypophysial or vegetative (area postrema) systems. They should therefore prevent the side effects of the existing compounds, related to the effect of the latter on the extrapyramidal, antehypophysial and vegetative areas. In addition, the D$_3$ partial agonist nature is such as to normalize the dopaminergic transmissions without the risk of excessive activation.

The derivatives of the invention can thus be used for the preparation of pharmaceutical compositions and medicaments for the treatment of neuropsychiatric conditions involving the D$_3$ receptor, such as psychotic or depressive states.

In addition, taking into account the role of the $D_3$ receptor in drug-dependence states, pharmaceutical compositions or medicaments based on these derivatives can be usefully administered in states related to abstinence and/or facilitate detoxification of subjects dependent on cocaine, heroin, alcohol, nicotine, and the like.

The derivatives according to the invention also have effects on penile erection and can also be used for the preparation of pharmaceutical compositions and medicaments for the treatment of disorders of a sexual nature, in particular male impotence.

The derivatives according to the invention, as well as, generally, agonists of the $D_3$ receptor, can also be used for a treatment complementary to the treatment of Parkinson's disease by L-DOPA. The invention thus relates to such complementary medicaments as well as to the use of agonists of the $D_3$ receptor, including the novel products of the present invention, for the preparation of a medicament for the complementary treatment of Parkinson's disease.

This activity could be explained by the discovery, with respect to an animal model of Parkinson's disease, that the treatment by L-DOPA induces the expression, in the cells of the striatum, of $D_3$ receptors which would underline the sensitization to the motor effects of L-DOPA.

The derivatives of formula (I) according to the invention can be administered in particular by the oral route in the form of a pharmaceutical composition.

The therapeutically useful doses vary with the various derivatives but, for the compound of Example 5, it may be specified that they lie between 0.05 and 5 mg/kg by the oral route.

We claim:

1. A 2-Naphthamide in the form of bases or of salts of a compound of the formula

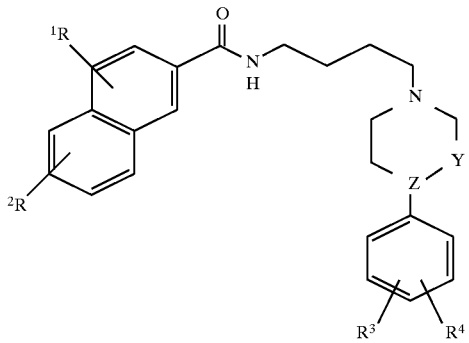

in which:

Z—Y is N—CH$_2$, $R^1$ is selected from the group consisting of hydrogen, fluorine, bromine, iodine, hydroxyl, methoxy, nitrile and nitro;

$R^2$ is selected from the group consisting of hydrogen, bromine, hydroxyl, methoxy, nitrile and nitro;

the $R_1$ and $R_2$ substituents both being situated on the same ring of the naphthamide unit or each being situated on one of the rings;

$R^3$ and $R^4$ are individually selected from the group consisting of hydrogen, chlorine, methoxy, methyl and an electron-withdrawing group.

2. Pharmaceutical composition, characterized in that it comprises a therapeutically effective amount of at least one compound according to claim 1, in base form or in the form of a pharmaceutically acceptable salt, in combination with a pharmaceutically acceptable vehicle or excipient.

3. Pharmaceutical composition, characterized in that it comprises a therapeutically effective amount of at least one compound according to claim 2, in base form or in the form of a pharmaceutically acceptable salt, in combination with a pharmaceutically acceptable vehicle or excipient.

4. A method of inducing a partial agonist of the activity of dopamine $D_3$ receptor in warm-blooded animals comprising administering to warm-blooded animals an amount of a compound of claim 1 sufficient to induce a partial angonistically effective activity of dopamine $D_3$ receptors.

5. A therapeutic composition comprising a partial agonistically effective amount of a dopamine $D_3$ receptor of a compound of claim 1 and an inert pharmaceutical carrier.

6. A therapeutic composition comprising a partial agonistically effective amount of a dopamine $D_3$ receptor of a compound claim 2 and an inert pharmaceutical carrier.

7. A method of claim 4 wherein the warm-blooded animal is a human suffering from Parkinson's disease and receiving treatment therefor.

8. Derivatives according to claim 1 selected from the group consisting of

N-[4-(4-(2-methoxyphenyl)piperazinyl)butyl]-1-methoxy-4-nitro-2-naphthamide;

N-[4-(4-(2-methoxyphenyl)piperazinyl)butyl]-1-methoxy-4-cyano-2-naphthamide;

N-[4-(4-(2-methoxyphenyl)piperazinyl)butyl]-2-naphthamide;

N-[4-(4-(2-chlorophenyl)piperazinyl)butyl]-3-methoxy-2-naphthamide;

N-[4-(4-(2-chlorophenyl)piperazinyl)butyl]-2-naphthamide;

N-[4-(4-(3-chlorophenyl)piperazinyl)butyl]-2-naphthamide;

N-[4-(4-phenylpiperazinyl)butyl]-2-naphthamide; and

N-[4-(4-(2-methoxyphenyl)piperazinyl)butyl]-1-methoxy-2-naphthamide oxalate.

9. A compound of claim 1 wherein $R_1$ is in the 1-position and is other than methoxy and $R_2$ is on the second ring of the naphthamide group.

10. A compound of claim 1 with no substituent in the 1-, 3- and 4-positions.

11. A compound of claim 1 wherein $R_1$ and $R_2$ are hydrogen.

12. The method of claim 4 selected from the group consisting of

N-[4-(4-(2-methoxyphenyl)piperazinyl)butyl]-1-methoxy-4-nitro-2-naphthamide;

N-[4-(4-(2-methoxyphenyl)piperazinyl)butyl]-1-methoxy-4-cyano-2-naphthamide;

N-[4-(4-(2-methoxyphenyl)piperazinyl)butyl]-2-naphthamide;

N-[4-(4-(2-chlorophenyl)piperazinyl)butyl]-3-methoxy-2-naphthamide;

N-[4-(4-(2-chlorophenyl)piperazinyl)butyl]-2-naphthamide;

N-[4-(4-(3-chlorophenyl)piperazinyl)butyl]-2-naphthamide;

N-[4-(4-phenylpiperazinyl)butyl]-2-naphthamide; and

N-[4-(4-(2-methoxyphenyl)pioperazinyl)butyl]-1-methoxy-2-naphthamide oxalate.

13. The method of claim 4 wherein $R_1$ is in the 1-position and is other than methoxy and $R_2$ is on the second ring of the naphthamide group.

14. The method of claim 4 with no substituent in the 1-, 3- and 4-positions.

15. The method of claim 4 wherein $R_1$ and $R_2$ are hydrogen.

* * * * *